United States Patent [19]

Kusase et al.

[11] Patent Number: 5,110,925

[45] Date of Patent: May 5, 1992

[54] PYRIDAZINONE DERIVATIVES

[75] Inventors: You Kusase; Masatoshi Murakata; Nobuo Mochizuki; Michinori Takebayashi, all of Odawara, Japan

[73] Assignee: Nippon Soda Co., Ltd., Japan

[21] Appl. No.: 427,123

[22] PCT Filed: Feb. 9, 1989

[86] PCT No.: PCT/JP89/00127

§ 371 Date: Oct. 4, 1989

§ 102(e) Date: Oct. 4, 1989

[87] PCT Pub. No.: WO89/07594

PCT Pub. Date: Aug. 24, 1989

[30] Foreign Application Priority Data

Feb. 13, 1988 [JP] Japan .................... 63-31618
Mar. 31, 1988 [JP] Japan .................... 63-75910

[51] Int. Cl.$^5$ ............................ C07D 237/26
[52] U.S. Cl. .......................... 544/234; 544/238; 544/239; 514/247; 514/250
[58] Field of Search .......... 544/239, 234, 240; 514/247

[56] References Cited

U.S. PATENT DOCUMENTS

| | | | |
|---|---|---|---|
| 4,019,575 | 5/1991 | Haikala | 514/247 |
| 4,665,174 | 12/1987 | Minai et al. | 564/305 |
| 4,681,621 | 7/1987 | Lee | 564/305 |
| 4,692,447 | 9/1987 | Cignarella | 544/234 |
| 4,775,411 | 10/1988 | Knudsen | 564/305 |
| 4,782,057 | 1/1988 | Tahara | 514/248 |
| 4,816,454 | 3/1989 | Zoeller et al. | 544/239 |
| 4,843,075 | 6/1989 | Nakao et al. | 544/234 |
| 4,849,421 | 7/1989 | Nakao et al. | 544/234 |
| 4,923,869 | 5/1990 | Prücher et al. | 544/239 |
| 4,954,501 | 9/1990 | Herter et al. | 544/239 |

FOREIGN PATENT DOCUMENTS

| | | | |
|---|---|---|---|
| 0084250 | 7/1983 | European Pat. Off. | |
| 0124314 | 11/1984 | European Pat. Off. | |
| 0129791 | 1/1985 | European Pat. Off. | |
| 0169443 | 1/1986 | European Pat. Off. | |
| 3302442 | 7/1984 | Fed. Rep. of Germany | |
| 57-46966 | 3/1982 | Japan | |
| 0216991 | 8/1989 | Japan | 544/234 |
| 2177689 | 1/1987 | United Kingdom | |

OTHER PUBLICATIONS

A. Davis et al. Jour. Comp. Aided Mol. Des, vol 1, pp. 97–120 (1987).
Patent Abst. of Japan, vol. 6, No. 11, C111 abstract of JP 57-46966 (1982).
Davis et al. Chem. Abstr. vol. 108 entry 48712j (1987).
Kusase et al. Chem. Abstr. vol. 112 entry 77210g.
H. R. Burmeister et al: "Moniliformin, a Metabolite or Fusarium moniliforme NRRL 6322, Purification and Toxicity", App. and Envir. Microbiol., vol 39 No. 1 (1979).

Primary Examiner—Donald G. Daus
Attorney, Agent, or Firm—Joseph C. Mason, Jr.

[57] ABSTRACT

The present invention relates to a compound having the formula below which have an excellent cardiotonic action:

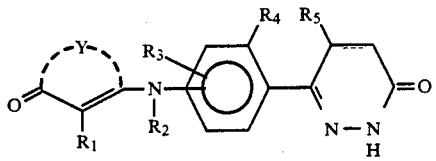

wherein Y represents $C_{1-4}$ alkylene which may be substituted by $C_{1-18}$ alkyl, $C_{1-5}$ alkoxy, $C_{1-5}$ alkylthio $C_{1-5}$ alkyl, $C_{1-5}$ alkoxycarbonyl or benzyl, or

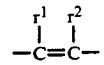

where each $r^1$ and $r^2$ represents hydrogen, $C_{1-18}$ alkyl, $C_{1-5}$ alkoxy, $C_{1-5}$ alkylthio $C_{1-5}$ alkyl, $C_{1-5}$ alkoxycarbonyl or benzyl); and $R_1$ represents hydrogen, $C_{1-5}$ alkyl which may be substituted by $C_{1-5}$ alkoxy, acetyl or $C_{2-5}$ alkenyl; and $R_2$ represents hydrogen or methyl; and each $R_3$ and $R_4$ represents hydrogen, halogen, hydroxy, $C_{1-5}$ alkyl, or $C_{1-5}$ alkoxy; and $R_5$ represents hydrogen or $C_{1-5}$ alkyl which may be substituted by hydroxy; and $R_4$ and $R_5$ may form ring by joining each other; and represents single or double bond.

1 Claim, No Drawings

PYRIDAZINONE DERIVATIVES

DESCRIPTION

1. Technical Field

The present invention relates to new pyridazinone derivatives and the process for the production of such compounds.

2. Background Art

Several drugs under development are known as cardiotonic drugs. The following compounds are typical examples:

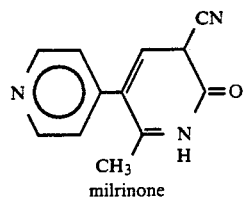
milrinone

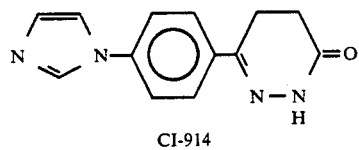
CI-914

The purpose of the present invention is to seek a new substance that has an excellent cardiotonic action and that is safe and free from side effects. It is also to offer the method in which this new substance can be manufactured in a commercially advantageous manner.

DISCLOSURE OF INVENTION

The present invention relates to a compound having the formula below, and the processes for the production of such compound:

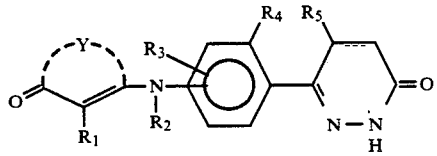

wherein

Y represents $C_{1-4}$ alkylene which may be substituted by $C_{1-18}$ alkyl, $C_{1-5}$ alkoxy, $C_{1-5}$ alkylthio, $C_{1-5}$ alkyl, $C_{1-5}$ alkoxycarbonyl or benzyl, or $$-\underset{\underset{r^1}{|}}{C}=\underset{\underset{r^2}{|}}{C}-$$

(where each $r^1$ and $r^2$ represents hydrogen, $C_{1-18}$ alkyl, $C_{1-5}$ alkoxy, $C_{1-5}$ alkylthio $C_{1-5}$ alkyl, $C_{1-5}$ alkoxycarbonyl or benzyl); and $R_1$ represents hydrogen, $C_{1-5}$ alkyl which may be substituted by $C_{1-5}$ alkoxy, acetyl or $C_{2-5}$ alkenyl; and $R_2$ represents hydrogen or methyl; and each $R_3$ and $R_4$ represents hydrogen, halogen, hydroxy, $C_{1-5}$ alkyl, or $C_{1-5}$ alkoxy; and $R_5$ represents hydrogen or $C_{1-5}$ alkyl which may be substituted by hydroxy; and $R_4$ and $R_5$ may form ring by joining each other; and represents single or double bond.

Compared to milrinone and CI-914, the compounds of the present invention exhibit a potent and selective inhibition of the phosphodiesterase III, have an excellent cardiotonic activity, are safe, non-toxic and orally effective, and are useful for the treatment of congestive heart failure. In addition, the compounds of the present invention inhibit a platelet aggregation and have an antithrombotic activity. The compounds of the present invention have a bronchodilatory activity and are useful for the treatment of chronic obstructive pulmonary disease such as asthma and bronchitis.

Moreover, the compounds of the present invention are useful for the treatment of various diseases (hypertension, ulcer, diabetes, cancer, etc.) which are associated with the intracellular level of cyclic AMP.

BEST MODE FOR CARRYING OUT THE INVENTION

The compounds under the present invention can be manufactured in the methods specified below.

(a) when $R_1$ is not acetyl;

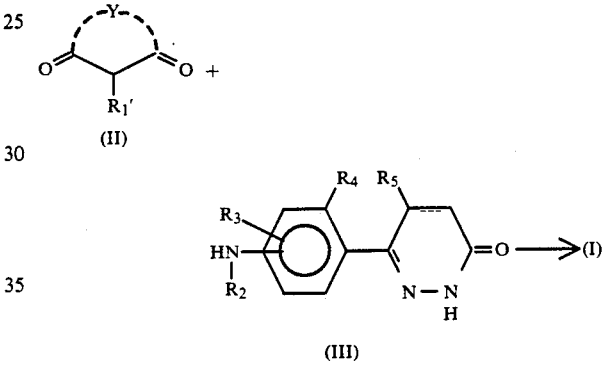

wherein $R'_1$ is hydrogen, $C_{1-5}$ alkyl which may be substituted by $C_{1-5}$ alkoxy, or $C_{2-5}$ alkenyl.

The reaction is carried out in an inert organic solvent, preferably in such a solvent as benzene, toluene, xylene, a lower alcohol or DMF, in the presence of an acid catalyst, preferably such a catalyst as hydrochloric acid, sulfuric acid, acetic acid or paratoluene sulfonic acid, at room temperature or by heating to a temperature above room temperature to 200° C. The reaction may be performed more efficiently if formed water is removed by such a means as azeotropic dehydration during the reaction.

(b) when $R_1$ is acetyl:

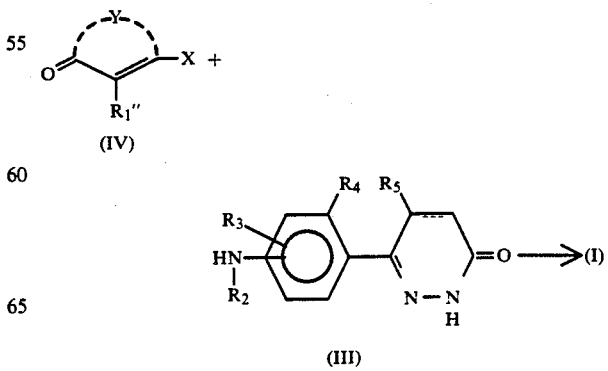

Wherein R''₁ is acetyl, and X is $C_{1-5}$ alkoxy.

The reaction is carried out in an inert organic solvent, preferably in such a solvent as a lower alcohol or DMF, at room temperature or by heating to a temperature above room temperature to 200° C. After the reaction is completed, a usual post-treatment gives the intended product.

The structure of the compounds of this invention has been determined from IR, NMR, MASS spectra, etc.

The compounds of this invention are expressed as pyridazinone-3(2H)-one compounds. However, the pyridazinone part can be a tautomer of pyridazinol, and if $R_2$ is hydrogen, the cycloacetylamino part be a tautom of enol form or keto form shown below.

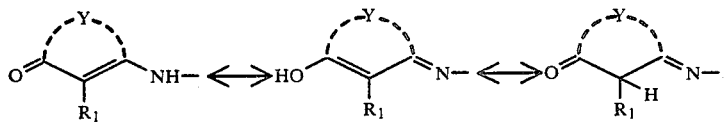

In addition, if $R_5$ is a methyl group and ⸺ is a single bond in the compound of this invention, an optical isomer is present. This invention includes all these isomers. Furthermore, each raw material having the formula (II), (III) or (IV) can be a similar tautomer.

The following Examples illustrate the present invention.

EXAMPLE 1

4,5-Dihydro-6-((4-(3-oxo-1-cyclopentenyl)amino)-phenyl)-3(2H)-pyridazinone (Compound No. 2)

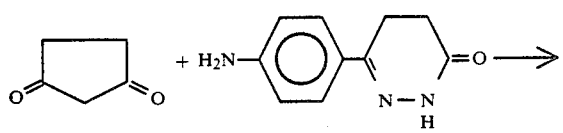

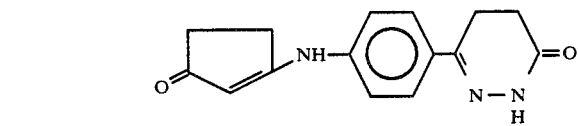

430 mg of 4,5-dihydro-6-(4-aminophenyl)-3(2H)-pyridazinone and 220 mg of cyclopentane-1,3-dione were suspended in 4 ml of ethanol, to which 2 ml of acetic acid was added. The resulting mixture was heated to reflux for 2 hours. After cooled, deposited crude crystal was collected by filtrating, and purified by silica gel column chromatography (eluting solvent: chloroform:methanol=10:1). 520 mg of the title compound was obtained. m.p.: >360° C. NMR (solvent: DMSO-d₆): δ 1.80-2.80 (m, 8H), 5.13 (S, 1H), 7.10 (dd, 4H), 9.33 (S, 1H), 10.50 (S, 1H).

EXAMPLE 2

4,5-Dihydro-6-(4-((2-methyl-3-oxo-1-cyclopentenyl)-amino)phenyl)-3(2H)-pyridazinone (Compound No. 4)

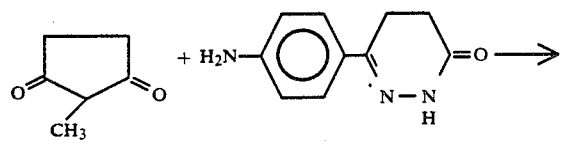

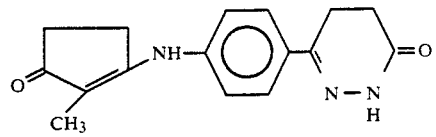

3.4 g of 4,5-dihydro-6-(4-aminophenyl)-3(2H)-pyridazinone and 2.0 of 2-methylcyclopentane-1,3-dione were suspended in 30 ml of toluene, to which a catalytic amount of p-toluene sulfonate-hydrate was add while the resulting suspension was heated to reflux with stirring for 8 hours, with removal of water as an azcotropic mixture. After cooled, deposited crude crystal was collected by filtrating, and purified by silica gel column chromatography (eluting solvent: chloroform::methanol=10:1), 4.7 g of the title compound was obtained. m.p. 284°-285° C.

EXAMPLE 3

3,5-Dihydro-6-(4-((2-acetyl-5,5-dimethyl-3-oxo-1-cyclohexenyl)amino)phenyl)-3(2H) pyridazinone (Compound No. 6)

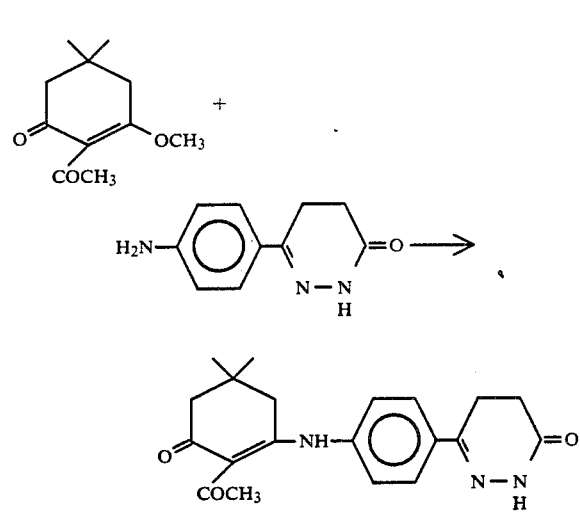

230 mg of 2-acetyl-5,5-dimethyl-3-methoxy-2-cyclohexene-1-one and 284 mg of 4,5-dihydro-6-(4-aminophenyl)-3(2H)-pyridazinone was suspended in 2 ml of ethanol, and the resulting mixture was heated to reflux for an hour. After cooled, crude crystal was collected by filtrating, and purified by silica gel column chromatography (eluting solvent: chloroform:methanol=30:1). 390 mg of the title compound was obtained. m.p. 212.0°-213.5° C.

EXAMPLE 4

4,5-Dihydro-6-(4-((3-oxo-1-cyclopentenyl)amino)-phenyl)-5-methyl-3(2H)-pyridazinone (Compound No. 14)

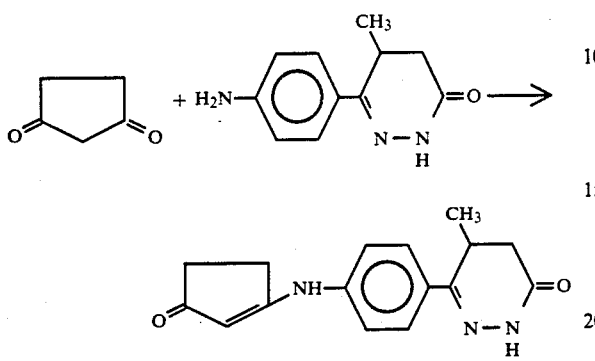

0.51 g of 4,5-dihydro-6-(4-aminophenyl)-5-methyl-3(2H)-pyridazinone and 0.25 g of cyclopentane-1,3-dione were suspended in a mixture of 5 ml of ethanol and 5 ml of acetic acid and the resulting suspension was refluxed for 7 hours. After cooled, deposited crude crystal was collected by filtrating and recrystallized from DMF-heptane-CHCl$_3$ to give 0.24 g of the title compound. m.p. >300° C. NMR (solvent DMSO-d$_6$-CDCl$_3$) δ 1.20 (d, 3H), 2.32–3.32 (m, 7H), 5.60 (S, 1H), 7.56 (dd, 4H), 9.82 (S, 1H), 10.80 (S, 1H).

EXAMPLE 5

4,5-Dihydro-6-(4-((2-methyl-3-oxo-1-cyclopentenyl)amino)phenyl)-5-methyl-3(2H)-pyridazinone (Compound No. 15)

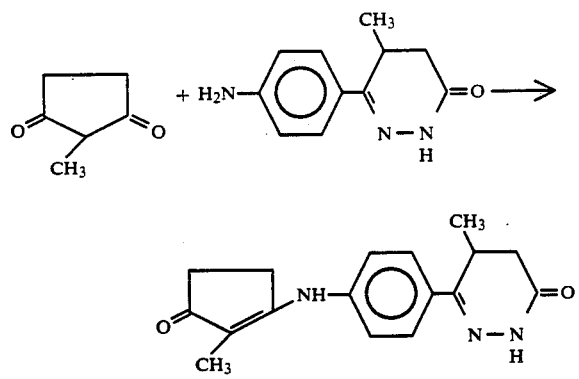

A mixture of 0.51 g of 4,5-dihydro-6-(4-aminophenyl)-5-methyl-3(2H) pyridazinone and 0.28 g of 2-methyl-cyclopentane-1,3-dione in 5 ml of ethanol and 5 ml of acetic acid was refluxed over night. After cooling, the solution was evaporated in vacuo. The residue was purified by silica gel column chromatography (eluting solvent: chloroform:methanol=20:1) and recrystallized from methanol to give 0.32 g of the title compound. m.p. 285°–286° C.

REFERENCE EXAMPLE 1

7-Acetamido-3-cyanomethylchroman-4-one

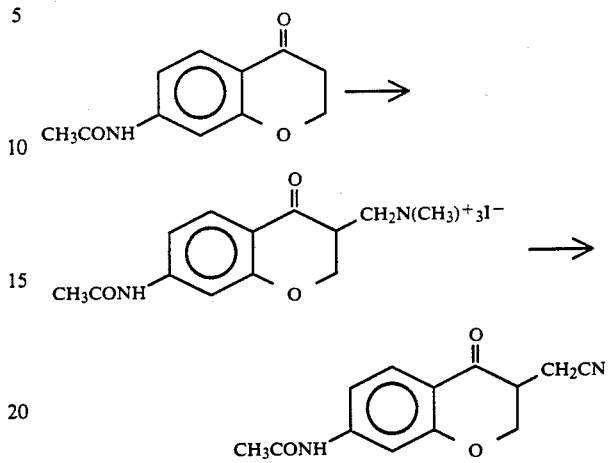

A mixture of 37% aqueous formaldehyde (1 ml) and dimethylamine hydrochloride (1.1 g) were stirred at room temperature for one hour.

After an addition of acetic anhydride (6 ml) the mixture was gradually heated until a one-phase system resulted.

To the solution 7-acetamidochroman-4-one (1.5 g, 7.3 m mole) was added, and the solution was heated (90°–100° C.) for one hour.

The solvent was removed under reduced pressure, acetone (20 ml) was added, and the solution was heated at reflux for 15 minutes. A residue obtained by evaporation of solvent under reduced pressure was dissolved in 1N aqueous NaOH (50 ml).

The solution was extracted with a mixture of chloroform/2-propanol (3:2) and the combined extracts were dried with anhydrous magnesium sulfate.

After remove of magnesium sulfate the solvent was evaporated to provide an oil.

After an addition of methyl iodide (2.8 g, 20 m mole) to the oil in acetone (50 ml), the solution was heated at reflux for one hour. After cooling the resulting solid was collected to provide the quaternary salt (1.78 g, yield 60.4%).

To a suspension of quaternary salt (510 mg, 1.26 m mole) in a mixture of methanol/water (1:1, 10 ml), potassium cyanide (100 ml, 1.54 m mole) in water (2 ml) was added.

The mixture was stirred at room temperature for eight hours. Then, the resulting solid was collected to provide 7-acetamido-3-cyanomethylchroman-4-one (200 mg. Yield 65.1%). (NMR (CD$_3$OD), δ: 2.13 (3H, S), 2.70–3.00 (2H, m), 4.10–4.83 (3H, m), 7.05 (1H, dd), 7.43 (1H, d), 7.73 (1H, d))

REFERENCE EXAMPLE 2

8-Amino-3,4,4a,5-tetrahydro-2H-(1)benzopyrano(4,3-c)pyridazin-3-one

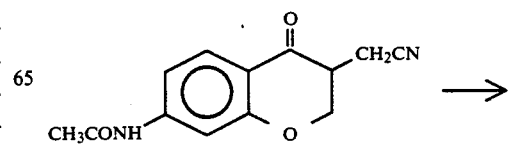

-continued

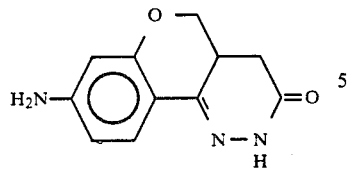

A suspension of 7-acetamido-3-cyanomethylchroman-4-one (200 mg, 0.82 m mole) in 6N aqueous HCl (8 ml) was heated at reflux for one hour. After cooling 6N aqueous NaOH was added until a solution was adjusted to pH 5, and 100% hydrazine hydrate (100 mg, 2 m mole) was added.

Then the solution was heated at reflux for 4 hours. After cooling the product was collected to provide 8-amino-3,4,4a,5-tetrahydro-2H-(1)benzopyrano(4,3-c)pyridazin-3-one (130 mg, yield 73.1%), m.p. 232°–235° C. (dec.)

EXAMPLE 6

8-(3-oxo-1-cyclopentenylamino)-3,4,4a,5-tetrahydro-2H-(1)benzopyrano(4,3-c)-pyridazinon-3-one (Compound No. 24)

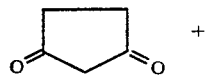 +

-continued

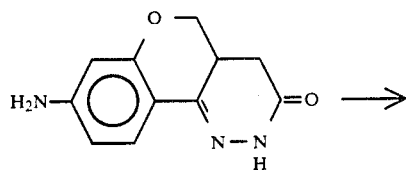

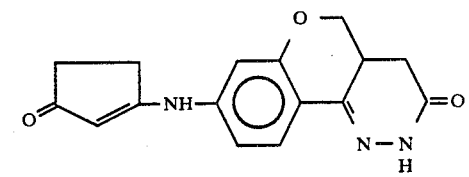

To a suspension of 8-amino-3,4,4a,5-tetrahydro-2H-(1)benzopyrano(4,3-c)pyridazin-3-one (130 mg, 0.6 m mol) in a mixture of ethanol/acetic acid (1:1, 2 ml), 1,3-cyclopentanedione (120 mg, 1.2 m mole) was added, and the suspension was heated at reflux for 4 hours.

A residue obtained by evaporation of solvent was chromatographed on silica gel (eluting solvent: chloroform:metanol=50:1) to provide the title compound (170 mg, yield 95%). m.p. 327° C. (dec.)

Inclusive the above, each compound within the scope of this invention which can be prepared in analogous method(s) is tabulated in Table 1.

TABLE 1

Structure Formula

| Compound No. | ---Y--- | °1' | $R_1$ | $R_2$ | $R_3$ | $R_4$ | $R_5$ | | Physical Properties ( ) m.p. °C. |
|---|---|---|---|---|---|---|---|---|---|
| 1 | —CH₂—C(CH₃)(CH₃)—CH₂— | 4-position | H | H | H | H | H | single bond | (272-274) |
| 2 | —CH₂CH₂— | " | " | " | " | " | " | " | (360 up) |
| 3 | —CH₂CH₂CH₂— | " | " | " | " | " | " | " | (252-254) |
| 4 | —CH₂CH₂— | " | CH₃ | " | " | " | " | " | (284-285) |
| 5 | —C(CH₃)(CH₃)—CH₂—CH₂— | " | H | " | " | " | " | " | (283-285) |
| 6 | —CH₂—C(CH₃)(CH₃)—CH₂— | " | COCH₃ | " | " | " | " | " | (212-213.5) |
| 7 | —CH(COOCH₃)—C(CH₃)(CH₃)—CH₂— | " | H | " | " | " | " | " | (189-191) |
| 8 | —CH₂—CH(CH₃)—CH₂— | " | " | " | " | " | " | " | (272-273.5) dec. |
| 9 | —CH₂—CH(OC₂H₅)— | " | " | " | " | " | " | " | (258-260) dec. |
| 10 | —CH₂—C(CH₃)(CH₃)—CH₂— | " | " | " | " | " | CH₃ | " | (282.5-284.5) |

TABLE 1-continued

Structure Formula

[Chemical structure shown with substituents $R_1$, $R_2$, $R_3$, $R_4$, $R_5$ on a fused ring system containing N, NH, and carbonyl groups; positions 1-6 labeled on the phenyl ring; Y group bridging]

| Compound No. | —Y— | *1' | $R_1$ | $R_2$ | $R_3$ | $R_4$ | $R_5$ | | Physical Properties ( ) m.p. °C |
|---|---|---|---|---|---|---|---|---|---|
| 11 | —CH$_2$—CH(C$_2$H$_5$)—CH$_2$— | " | " | " | " | " | H | " | (257–260) |
| 12 | —CH$_2$—CH(C$_3$H$_7$)—CH$_2$— | 4-position | H | H | H | H | H | single bond | (270–272) |
| 13 | —CH$_2$CH$_2$CH$_2$— | " | " | " | " | " | CH$_3$ | " | (263.5–266) |
| 14 | —CH$_2$CH$_2$— | " | " | " | " | " | " | " | (300 up) |
| 15 | " | " | CH$_3$ | " | " | " | " | " | (285–286) |
| 16 | —CH$_2$—C(CH$_3$)(CH$_3$)—CH$_2$— | " | H | " | " | " | H | double bond | (302–305) |
| 17 | —CH$_2$CH$_2$CH$_2$— | " | " | " | " | " | " | " | (273–276) |
| 18 | —CH$_2$CH$_2$— | " | " | " | " | " | " | " | (340 up) |
| 19 | " | " | " | " | " | " | C$_2$H$_5$ | single bond | (300 up) |
| 20 | " | 3-position | " | " | 4-CH$_3$ | " | H | " | (241–244) |
| 21 | " | 4-position | " | CH$_3$ | H | " | " | " | (251–253) |
| 22 | —CH$_2$—CH(C$_4$H$_9$)—CH$_2$— | " | " | H | " | " | " | " | (261.5–263) |
| 23 | —CH$_2$—CH(C$_5$H$_{11}$)—CH$_2$— | " | " | " | " | " | " | " | (256–258) |
| 24 | —CH$_2$CH$_2$— | " | " | " | " | —OCH$_2$— | " | (327) dec. |
| 25 | —CH$_2$CH$_2$CH$_2$— | " | " | CH$_2$CH=CH$_2$ | " | H | H | " | (197–198) |
| 26 | —CH$_2$CH$_2$— | " | " | CH$_3$ | " | —OCH$_2$— | " | (280–281.5) |
| 27 | —CH$_2$CH$_2$CH$_2$— | " | " | C$_3$H$_7$ | " | H | H | " | (222–223) |
| 28 | " | " | " | C$_2$H$_5$ | " | " | " | " | (237–238) |
| 29 | " | " | " | C$_4$H$_9$ | " | " | " | " | (174–175) |
| 30 | —CH$_2$—CH(C$_7$H$_{15}$)—CH$_2$— | 4-position | H | H | H | H | H | single bond | (258.5–260) |
| 31 | —CH$_2$—CH(C$_{10}$H$_{21}$)—CH$_2$— | " | " | " | " | " | " | " | (260–261) |
| 32 | —CH$_2$CH(CH$_2$C$_6$H$_5$)CH$_2$— | " | " | " | " | " | " | " | (238–240) |
| 33 | —CH$_2$—CH[C(CH$_3$)(CH$_3$)(SCH$_3$)]—CH$_2$— | " | " | " | " | " | " | " | (300 up) |
| 34 | —CH$_2$CH$_2$— | " | " | CH$_2$CH=CH$_2$ | " | " | " | " | (162–163) |
| 35 | " | " | " | H | " | " | —CH$_2$CH$_2$— | " | (300 up) |
| 36 | " | " | " | CH$_3$ | " | " | " | " | (263–264) |
| 37 | " | " | 3-position | H | " | " | H | H | " | (276–277) |
| 38 | " | " | " | CH$_3$ | " | " | " | " | (276–277) |
| 39 | " | " | 4-position | H | " | 3-CH$_3$ | " | " | " | (230–231) |
| 40 | " | " | " | CH$_3$ | " | " | " | " | (217–218) |
| 41 | " | " | " | H | " | H | —CH$_2$— | " | (305) dec. |
| 42 | " | " | 2-position | " | " | 4-CH$_3$O | H | H | " | (242) dec. |
| 43 | " | " | 4-position | CH$_3$ | " | H | —CH$_2$— | " | (313–314) dec. |
| 44 | —CH$_2$CH$_2$CH$_2$— | 4-position | H | H | H | —CH$_2$— | single bond | (292–294) dec. |
| 45 | —CH$_2$CH$_2$— | " | " | CH$_3$ | " | 3-Cl | H | H | " | (115–116) |
| 46 | " | " | " | " | " | 3-Br | " | " | " | (104.5–106.5) |
| 47 | " | " | " | H | H | 3-CH$_3$O | " | " | " | (260–261) |
| 48 | " | " | " | " | " | 2-CH$_3$O | " | " | " | (220) dec. |

TABLE 1-continued

Structure Formula

[Structure with R3, R4, R5 on benzene ring connected to N—NH and =O group, with Y, R1, R2 substituents]

| Compound No. | ---Y--- | *1' | R1 | R2 | R3 | R4 | R5 | | Physical Properties ( ) m.p. °C. |
|---|---|---|---|---|---|---|---|---|---|
| 49 | " | " | " | CH₃ | H | " | CH₃ | " | (216–220) |
| 50 | " | " | " | H | 2-OH | " | H | " | (280) dec. |
| 51 | " | " | CH₃ | CH₃ | H | " | CH₃ | " | (200–205) |
| 52 | " | " | " | H | " | " | " | double bond | (270) dec. |
| 53 | " | " | H | " | " | " | HOCH₂ | single bond | (224) dec. |

*1: Substituted position of $-\overset{R_2}{\underset{|}{N}}-$ in the benzene ring

INDUSTRIAL APPLICABILITY

The pharmacological effects in the compounds of the present invention is described by the following tests.

TEST 1

Cardiotonic Action: Electrically Stimulating Isolated Guinea Pig Left Atria

Male Hartley guinea pigs weighing 350–500 g were used.

The hearts were excised from the animals. The left atria were dissected from the hearts and mounted in an organ bath.

The bath was filled with 50 ml oxygenated (95% $O_2$ and 5% $CO_2$) Krebs-Henseleit solution at 30° C. of the following composition: NaCl 118 mM; KCl 4.7 mM; $CaCl_2.2H_2O$ 2.5 mM; $MgSO_4.7H_2O$ 1.2 mM; $KH_2PO_4$ 1.2 mM; $NaHCO_3$ 25.0 mM; glucose 10.0 mM.

The atria were stimulated by square wave pulses of 3 msec duration and a voltage ranging from 1.2-fold to 1.5-fold of the threshold at a frequency of 60/min with an electric stimulator.

Resting tension was adjusted to 0.5 g and contraction was recorded on the Polygraph Systems with a force-displacement transducer.

All preparations were allowed to equilibrate with the bath medium for 90 to 120 min.

The test compounds were added cumulatively to the bath and the concentrations causing a 50% increase in contractility ($EC_{50}$) were calculated from the concentration-response curves.

The results are shown in Table 2.

TABLE 2

| Compound No. | contractility of guinea pig left atria $EC_{50}$ (μg/ml) |
|---|---|
| 1 | 0.23 |
| 2 | 0.11 |
| 3 | 0.23 |
| 4 | 0.24 |
| 14 | 0.12 |
| 15 | 0.054 |
| Milrinone | 0.43 |
| CI-914 | 1.8 |

TEST 2

Cardiotonic Action: Anesthetized Dogs

Adult mongrel dogs of either sex weighing 8 to 15 kg were used.

The animals were anesthetized with sodium pentobarbital (30 mg/kg, i.v.) and maintained by an intravenous infusion of the anesthetic at a rate of 4 mg/kg per hour.

A cuffed endotracheal tube was inserted and an artificial respirator installed. The animals were ventilated with room air in a tidal volume of 20 ml/kg at a rate of 20 brearhs per minute.

Cannulae were inserted into the femoral vein for a falling drop of a physiological saline or for an infusion of the anesthetic, and into the femoral artery for measuring arterial blood pressure with a pressure transducer. Heart rate was recorded with a heart rate counter triggered by the R wave of the electrocardiogram (ECG).

ECG in standard lead II was monitored with a bioelectric amplifier.

Left ventricular pressure was measured with a catheter tip pressure transducer inserted via the right carotid artery into the left ventricle. Left ventricular $dp/dt_{max}$ was obtained by an electric differentiator.

The compounds were injected through the cannula in the femoral vein at a dose of 0.001–0.3 mg/0.1 ml/kg.

The doses producing a 50% increase in $LVdp/dt_{max}$ ($ED_{50}$) were calculated from the dose-response curves.

The results are shown in Table 3.

TABLE 3

| Compound No. | $LVdp/dt_{max}$ $ED_{50}$ (μg/kg,i.v.) | % Changes in Heart rate | % Changes in Blood pressure |
|---|---|---|---|
| 1 | 43 | 5 | −1 |
| 2 | 6 | 6 | −2 |
| 3 | 9 | 2 | −4 |
| 4 | 12 | 5 | −2 |
| 14 | 8 | 13 | −11 |
| 15 | 12 | 19 | −18 |
| 24 | 22 | 4 | −7 |
| 26 | 30 | 8 | −6 |
| 35 | 23 | 3 | −4 |
| Milrinone | 23 | 6 | −6 |
| CI-914 | 95 | 9 | −10 |

TEST 3

Inhibition of Phosphodiesterase

The preparation of different forms of cyclic nucleotide phosphodiesterase from guinea pig left ventricular muscles was done by following the procedure of Weishaar, et al. (R. Weishaar, et al., Biochemical Pharmacology, 35, 787–800, 1986) with the minor modified method of Thompson, et al. (W. J. Thompson, et al., Advances in Cyclic Nucleotide Research, 10, 69-92, 1979). Briefly, the three active forms of phosphodiesterase (PDE-I, PDE-II, PDE-III) present in the ventricular muscles were discretely eluted from a DEAE-cellulose column (Whatman, DE-52, $\phi$ 2.5×20 cm) using a continuous 70–800 mM sodium acetate gradient.

The phosphodiesterase activity was assayed by minor modifications of the method described by Furutani et al. (Y. Furutani, et al., Journal of Antibiotics, 28, 558-560, 1975). Briefly, 1 mM $^3$H-cAMP was hydrolyzed by the phosphodiesterase and the unhydrolyzed $^3$H-cAMP which was separated from the formed 5'-AMP by a dry alumina (Merck, activity 1, neutral) was counted by a liquid scintillation counter.

The concentrations causing a 50% inhibition of the phosphodiesterase activity (IC$_{50}$) were calculated from the concentration-inhibition curves.

The results are shown in Table 4.

TABLE 4

| Compound No. | phosphodiesterase inhibition IC$_{50}$ ($\mu$M) | | |
| --- | --- | --- | --- |
| | PDE-I | PDE-II | PDE-III |
| 1 | 900 | 250 | 1.2 |
| 2 | 1000 | 235 | 1.2 |
| 3 | 210 | 180 | 0.47 |
| 4 | 610 | 330 | 2.0 |
| 14 | 310 | 260 | 0.88 |
| 15 | >1000 | 940 | 0.59 |
| 24 | >100 | 100 | 4.1 |
| 26 | >1000 | 100 | 2.3 |
| 35 | >100 | 49 | 1.6 |
| Milrinone | 151 | 142 | 2.8 |
| CI-914 | >1000 | 276 | 5.7 |

TEST 4

Acute Toxicity

The acute toxicity of the test compounds was studied in male mice after oral administration of a single dose. The animals were observed for 7 days and the mortality was determined.

The results are shown in Table 5.

TABLE 5

| | acute toxicity in mice, 300 mg/kg.p.o. mortality (number of dead animals/ |
| --- | --- |
| Compound No. | number of treated animals) |
| 1 | 0/3 |
| 2 | 0/3 |
| 3 | 0/3 |
| 4 | 1/3 |
| Milrinone | 3/3 |
| CI-914 | 2/3 |

We claim:
1. A compound of the formula

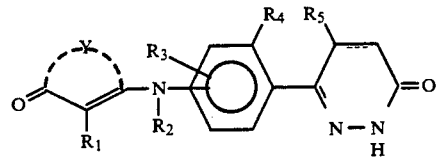

wherein
Y represents C$_{2-3}$ alkylene which may be substituted by one gemdimethyl and/or one C$_{1-10}$ alkyl, C$_{1-2}$ alkoxy, benzyl, methylthio C$_{1-3}$ alkyl or C$_{1-2}$ alkoxycarbonyl;
R$_1$ represents hydrogen, C$_{1-4}$ alkyl, acetyl or allyl;
R$_2$ represents hydrogen or methyl;
R$_3$ represents hydrogen, methyl, methoxy, halogen or hydroxy;
R$_4$ represents hydrogen;
R$_5$ represents hydrogen or C$_{1-2}$ alkyl which may be substituted by hydroxy;
R$_4$ and R$_5$ may form —OCH$_2$—, —CH$_2$CH$_2$— or —CH$_2$— by joining each other; and
represents single or double bond; or a pharmaceutically acceptable salt thereof.

* * * * *